(12) United States Patent
Ohta et al.

(10) Patent No.: US 7,680,623 B2
(45) Date of Patent: Mar. 16, 2010

(54) MEASURING SYSTEM, COMPUTING DEVICE AND COMPUTER READABLE MEDIUM HAVING PROGRAM EXECUTING TO PERFORM MEASURING A REGION-IN-OBJECT

(75) Inventors: Naoya Ohta, Maebashi (JP); Kenji Mogi, Maebashi (JP); Yoshiki Nakasone, Maebashi (JP)

(73) Assignee: National University Corporation Gunma University, Gunma (JP)

( * ) Notice: Subject to any disclaimer, the term of this patent is extended or adjusted under 35 U.S.C. 154(b) by 21 days.

(21) Appl. No.: 11/722,174

(22) PCT Filed: Dec. 21, 2005

(86) PCT No.: PCT/JP2005/023992

§ 371 (c)(1),
(2), (4) Date: Apr. 10, 2008

(87) PCT Pub. No.: WO2006/068285

PCT Pub. Date: Jun. 29, 2006

(65) Prior Publication Data

US 2008/0275666 A1   Nov. 6, 2008

(30) Foreign Application Priority Data

Dec. 21, 2004  (JP) .............................. 2004-369900
Aug. 10, 2005  (JP) .............................. 2005-232161

(51) Int. Cl.
*G06F 15/00* (2006.01)
*A61B 6/00* (2006.01)

(52) U.S. Cl. .......................................... 702/150; 378/4
(58) Field of Classification Search ................. 702/150, 702/152, 153, 155, 156; 382/128, 130, 154; 378/4

See application file for complete search history.

(56) References Cited

U.S. PATENT DOCUMENTS 5,964,715 A    10/1999  Thunberg .................... 600/562
2004/0161137 A1*  8/2004  Aben et al. ................. 382/128

FOREIGN PATENT DOCUMENTS

| JP | 58-065142 | 4/1983 |
| JP | 03-010151 | 1/1991 |
| JP | 07-092111 | 4/1995 |
| JP | 09-187448 | 7/1997 |

(Continued)

OTHER PUBLICATIONS

Radeva, et al., "3D Vessel Reconstruction From Biplane Angiograms Using Snakes" Computers in Cardiology, vol. 25, pp. 773-776, 1998.

(Continued)

*Primary Examiner*—Bryan Bui
(74) *Attorney, Agent, or Firm*—Hogan & Hartson LLP

(57) ABSTRACT

A region-in object measuring system comprises a reference object (1) having two frames, i.e., an object surface frame (2) brought into contact with the surface of an object and a film frame (3) with which an X-ray film (7) is brought into contact, spaced from each other and a computing device. The computing device sets a three-dimensional X-ray coordinate system using the reference object (1) according to a two-dimensional X-ray image acquired by imaging a region in an object in a state that the object surface frame (2) of the reference object (1) is in close contact with the surface of the object by means of an X-ray imaging apparatus, determining the position of an X-ray source from the projection magnification and size of the image of the object surface frame (2), determining the position vector of a specific region in a body according to the position of the X-ray source, and accurately determines the direction and three-dimensional position of the region in the object with respect to the position of the image of the region in the object shown on the X-ray image.

17 Claims, 10 Drawing Sheets

FOREIGN PATENT DOCUMENTS

| JP | 10-201749 | 8/1998 |
| JP | 2004-337538 | 12/2004 |
| JP | 2004-350767 | 12/2004 |

OTHER PUBLICATIONS

Kita, et al., "Correspondence Between Different View Breast X Rays Using Curved Epipolar Lines" Computer Vision and Image Understanding, vol. 83, No. 1, pp. 38-55, 2001.

Wan, et al., "SMIS—A Real-Time Stereoscopic Medical Imaging System" Proceedings of the 17$^{th}$ IEEE Symposium on Computer-Based Medical Systems, pp. 197-202, 2004.

Evans, et al., "A New Stereoscopic X-Ray Imaging Technique Using a Single X-Ray Source: Theoretical Analysis" Journal of Non-Destructive Testing and Evaluation International, pp. 27-35, Feb. 1996.

Evans, et al., "Pseudo-Tomographic X-Ray Imaging for Use in Aviation Security" IEEE Aerospace and Electronics Systems Magazine, Bol. 13, No. 7, pp. 25-30, 1998.

* cited by examiner

MEASURING SYSTEM, COMPUTING DEVICE AND COMPUTER READABLE MEDIUM HAVING PROGRAM EXECUTING TO PERFORM MEASURING A REGION-IN-OBJECT

CROSS-REFERENCE TO THE RELATED APPLICATIONS

This application is a national phase of the international application No. PCT/JP2005/023992 filed Dec. 21, 2005, which also claims benefit of priority under 35 U.S.C. § 119 to Japanese Patent Application No. 2004-369900 filed Dec. 21, 2004 and Japanese Patent Application No. 2005-232161 filed Aug. 10, 2005, the entire contents of which are incorporated by reference.

TECHNICAL FIELD

The present invention relates to a region-in-object measuring system, a computing device for measuring a region-in-object, a program for measuring a region-in-object and a computer readable recording medium on which the program is recorded. More specifically, the present invention relates to a novel region-in-object measuring system, a computing device for measuring a region-in-object, a program for measuring a region-in-object and a computer readable recording medium on which the program is recorded, using a two-dimensional X-ray photograph to accurately determine the orientation or the location of a particular region inside an object.

BACKGROUND ART

Generally, it is sometimes desired to determine the location and the orientation of a particular region inside an object from outside the object. For a specific medical example, there is an injection in a mental foramen in the operation of oral surgery. The mental foramen is a hole of a few millimeters in a skull through which nerves pass. In some treatment, the necessity occurs that a drug is injected into a mental foramen by injection. For that injection, it is necessary to specify the location and the orientation of the mental foramen through the surface of an object (the skin surface in this case). However, in typical X-ray photography (x-ray radiography), only the relative two-dimensional shape of the internal tissue can be known.

For an apparatus which allows three-dimensional measurement of the particular region inside an object including a body, there is a CT apparatus. However, the CT apparatus is a very expensive apparatus, and in the use case considered here as an example, there are problems of large effort required for measurement and a great X-ray radiation exposure to a patient.

On the other hand, JP-A-S58-65142 discloses an imaging diagnostic apparatus in which an X-ray imaging apparatus is provided that takes a front image and a side image with X-rays, the two images are shown on a display, the region of interest is indicated by a light pen to show an elliptic front image and a rotating elliptic side image of the region of interest, and the rough shape and the location of the region of interest are known three-dimensionally.

In addition, JP-A-H03-10151 discloses an object inspection apparatus in which, X-rays are applied from different directions while a target object for inspection is being moved at a predetermined rate, and a failure area in a target object for measurement is inspected three-dimensionally based on image signals of X-rays having passed through the target object for inspection.

In addition, JP-A-H07-92111 discloses a defect test apparatus in which a target object for inspection is fixed, an X-ray source is moved to allow X-rays to transmit from two places, and the depth of a defect part of the target object for inspection is detected using the difference between the amounts of X-ray transmission.

Moreover, JP-A-H09-187448 discloses an X-ray imaging diagnostic apparatus in which X-ray images are taken from a plurality of directions, quantitative analysis is performed for a diagnosed area such as a blood vessel and a heart of a target object based on the X-ray images, and the diagnosed area is known three-dimensionally in consideration of error caused by fluctuations in the depth orientation.

DISCLOSURE OF THE INVENTION

However, the scheme disclosed in JP-A-S58-65142 is a scheme in which the region of interest is known three-dimensionally based on the image signals of the X-ray photographs taken from the front and the side so as to include the region of interest inside the body. Although the shape and the location of the region of interest can be roughly known by the scheme, the scheme is not suited for the purpose of accurately knowing the orientation and the location of the particular region inside the body in order for injection in the mental foramen as described above.

In addition, the scheme disclosed in JP-A-H03-10151 is a scheme of inspecting a defect of a ceramic substrate, for example. Since X-rays are applied while the target object for inspection is being moved at a predetermined rate, it is not suited for the purpose of accurately knowing the orientation and the location of the particular region inside a body.

In addition, the scheme disclosed in JP-A-H07-92111 is a scheme of nondestructive inspection of defects in a plant, for example. There is also a problem of the amount of exposure, and it is not suited for the purpose of accurately knowing the orientation and the location of the particular region inside a body as well.

Moreover, the scheme disclosed in JP-A-H09-187448 is a scheme in which in order to know the degree of a disease of a blood vessel and a heart, for example, the depth orientation is corrected based on the images taken from two directions with X-rays, and the state of the diagnosed area is known three-dimensionally. However, it is not suited for the purpose of accurately knowing the orientation and the location of the particular region inside a body with respect to the reference position of the surface of the object for the purpose of injection in the mental foramen, for example.

Then, the present invention has been made in view of the circumstances. An object of the present invention is to provide a region-in-object measuring system, a computing device for measuring a region-in-object, a program for measuring a region-in-object and a computer readable recording medium on which the program is recorded, in which three-dimensional information of a particular region such as the orientation and the location of the mental foramen with respect to a reference position on the surface (skin) of an object can be accurately determined at low costs as effort required for measurement and an X-ray radiation exposure to a patient are suppressed as much as possible.

In addition, the technique according to the present invention can be utilized not only for measuring the inside of a body but also for measuring the inside of a general object. Therefore, it is also an object of the present invention to provide a convenient method of measuring the location of the particular region of a general object.

According a first aspect of the invention, in order to solve the above problems, there is provided a region-in-object measuring system comprising: a reference object having an object surface frame which is closely contacted with a surface of an object and a film frame which is closely contacted with an X-ray film, the two frames being separated from each other; and a computing device having: an input part which captures a two-dimensional X-ray image obtained by imaging a region-in-object by means of an X-ray imaging apparatus in a state in which the object surface frame of the reference object is closely contacted with the surface of the object; a first computing part which determines a projection scaling factor for an image of the object surface frame based on the size of a predetermined pattern on a plane of the object surface frame and the size of an image of a predetermined pattern in a two-dimensional X-ray image; a second computing part which determines a position vector of a specific point on the plane of the object surface frame and a position vector of an image of a specific point on the plane of the object surface frame in the two-dimensional X-ray image; a third computing part which determines a position vector of an X-ray source based on the projection scaling factor determined by the first computing part and the position vector of the specific point on the plane of the object surface frame and the position vector of the image of the specific point on the plane of the object surface frame determined by the second computing part; a fourth computing part which determines a position vector of an image of the region-in-object in the two-dimensional X-ray image; and a fifth computing part which determines a position vector of the region-in-object based on the position vector of the X-ray source determined by the third computing part and the position vector of the image of the region-in-object determined by the fourth computing part, and which decides an orientation of the region-in-object with respect to the location of the image region-in-object.

According to a second aspect of the invention, there is provided a region-in-object measuring system comprising: a reference object having an object surface frame which is closely contacted with a surface of an object and a film frame which is closely contacted with an X-ray film, the two frames being separated from each other; and a computing device having: an input part which captures two or more of two-dimensional X-ray images obtained by imaging a region-in-object from different directions by means of an X-ray imaging apparatus in a state in which the object surface frame of the reference object is closely contacted with the surface of the object; a first computing part which determines a projection scaling factor for an image of the object surface frame based on the size of a predetermined pattern on a plane of the object surface frame and the size of an image of a predetermined pattern in a two-dimensional X-ray image; a second computing part which determines a position vector of a specific point on the plane of the object surface frame and a position vector of an image of a specific point on the plane of the object surface frame in the two-dimensional X-ray image; a third computing part which determines a position vector of an X-ray source based on the projection scaling factor determined by the first computing part and the position vector of the specific point on the plane of the object surface frame and the position vector of the image of the specific point on the plane of the object surface frame determined by the second computing part; a fourth computing part which determines a position vector of an image of the region-in-object in the two-dimensional X-ray image; a fifth computing part which determines a position vector of the region-in-object based on the position vector of the X-ray source determined by the third computing part and the position vector of the image of the region-in-object determined by the fourth computing part; and a sixth computing part which decides a three-dimensional location of the region-in-object based on two or more of position vectors of the region-in-object determined by the fifth computing part.

According to a third aspect of the invention, there is provided a region-in-object measuring system comprising: a reference object having an object surface frame which is closely contacted with a surface of an object and a film location reference frame which is a reference of an X-ray film placed at a free location, the two frames being separated from each other; and a computing device having: an input part which captures a two-dimensional X-ray image obtained by imaging a region-in-object by means of an X-ray imaging apparatus in a state in which the object surface frame of the reference object is closely contacted with the surface of the object; a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient; a second computing part which determines a projection scaling factor for the image of the object surface frame based on the size of a predetermined pattern on a plane of the object surface frame reference plane and the size of an image of a predetermined pattern on the reference plane; a third computing part which determines a position vector of a specific point on the plane of the object surface frame and a position vector of the specific point on the reference plane; a fourth computing part which determines a location of an X-ray source vector based on the projection scaling factor determined by the second computing part and the position vector of a specific point on the plane of the object surface frame and the position vector of an image of the specific point on the reference plane determined by the third computing part; a fifth computing part which determines a position vector of an image of the region-in-object on the reference plane; and a sixth computing part which determines a position vector of the region-in-object based on the location of the X-ray source vector determined by the fourth computing part and the position vector of the image of the region-in-object determined by the fifth computing part, and which decides an orientation of the region-in-object with respect to the location of the image region-in-object.

According to a fourth aspect of the invention, there is provided a region-in-object measuring system comprising: a reference object having an object surface frame which is closely contacted with a surface of an object and a film location reference frame which is a reference of an X-ray film placed at a free location, the two frames being separated from each other; and a computing device having: an input part which captures two or more of two-dimensional X-ray images obtained by imaging a region-in-object from different directions by means of an X-ray imaging apparatus in a state in which the object surface frame of the reference object is closely contacted with the surface of the object; a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient; a second computing part which determines a projection scaling factor for the image of the object surface frame based on the size of a predetermined pattern on a plane of the object surface frame and the size of an image of a predetermined pattern on the reference plane; a third computing part which determines a position vector of a specific point on the plane of the object surface frame and a position vector of an image of a specific point on the reference plane; a fourth computing part which determines a location of an X-ray source vector based on the projection scaling factor determined by the second computing part and the position vector of a specific point on the plane of the object surface frame and the position vector of an image of the specific point on the reference plane determined by the third computing part; a fifth computing part which determines a position vector of an image of the region-in-object on the reference plane; a sixth computing part which determines a position vector of the region-in-object based on the location of the X-ray source vector determined by the fourth computing part and the position vector of the image of the region-in-object determined by the fifth computing part; and a seventh computing part which decides a three-dimensional location of the region-in-object based on two or more of position vectors of the region-in-object determined by the sixth computing part.

According to a fifth aspect of the invention, there is proposed the region-in-object measuring system as described in the first or second invention, further comprising an X-ray imaging apparatus.

According to a sixth aspect of the invention, there is provided the region-in-object measuring system as described in any one of the first to fifth inventions, wherein an X-ray camera is used for imaging instead of using an X-ray film.

According to a seventh aspect of the invention as described in any one of the first to sixth inventions, wherein a reference object has a square object surface frame and a square film frame or a film location reference frame in the same size.

According to an eighth aspect of the invention there is provided a computing device for measuring a region-in-object comprising: an input part which captures a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface of the object and a film frame which is closely contacted with an X-ray film, and the two frames being separated from each other; a first computing part which determines a projection scaling factor for an image of the object surface frame based on the size of a predetermined pattern on a plane of the object surface frame and the size of an image of a predetermined pattern in a two-dimensional X-ray image; a second computing part which determines a position vector of a specific point on the plane of the object surface frame and a position vector of an image of a specific point on the plane of the object surface frame in the two-dimensional X-ray image; a third computing part which determines a position vector of an X-ray source based on the projection scaling factor determined by the first computing part and the position vector of the specific point on the plane of the object surface frame and the position vector of the image of the specific point on the plane of the object surface frame determined by the second computing part; a fourth computing part which determines a position vector of an image of the region-in-object in the two-dimensional X-ray image; and a fifth computing part which determines a position vector of the region-in-object based on the position vector of the X-ray source determined by the third computing part and the position vector of the image of the region-in-object determined by the fourth computing part, and which decides an orientation of the region-in-object with respect to the image of the region-in-object.

According to a ninth aspect of the invention, there is provided a computing device for measuring a region-in-object comprising: an input part which captures two or more two-dimensional X-ray images obtained by imaging a region-in-object from different directions by means of an X-ray imaging apparatus in a state in which an object surface frame of a reference object is closely contacted with a surface of the object, the reference object having the object surface frame which is closely contacted with the surface of the object and a film frame which is closely contacted with an X-ray film, and the two frames being separated from each other; a first computing part which determines a projection scaling factor for an image of the object surface frame based on the size of a predetermined pattern on a plane of the object surface frame and the size of an image of a predetermined pattern in a two-dimensional X-ray image; a second computing part which determines a position vector of a specific point on the plane of the object surface frame and a position vector of an image of a specific point on the plane of the object surface frame in the two-dimensional X-ray image; a third computing part which determines a position vector of an X-ray source based on the projection scaling factor determined by the first computing part and the position vector of the specific point on the plane of the object surface frame and the position vector of the image of the specific point on the plane of the object surface frame determined by the second computing part; a fourth computing part which determines a position vector of an image of the region-in-object in the two-dimensional X-ray image; a fifth computing part which determines a position vector of the region-in-object based on the position vector of the X-ray source determined by the third computing part and the position vector of the image of the region-in-object determined by the fourth computing part; and a sixth computing part which decides a three-dimensional location of the region-in-object based on two or more of position vectors of the region-in-object determined by the fifth computing part.

According to a tenth aspect of the invention, there is provided a computing device for measuring a region-in-object comprising: an input part which captures a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other; a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient; a second computing part which determines a projection scaling factor for the image of the object surface frame based on the size of a predetermined pattern on a plane of the object surface frame and the size of an image of a predetermined pattern on the reference plane; a third computing part which determines a position vector of a specific point on the plane of the object surface frame and a position vector of an image of the specific point on the reference plane; a fourth computing part which determines a location of an X-ray source vector based on the projection scaling factor determined by the second computing part and the position vector of a specific point on the plane of the object surface frame and the position vector of an image of the specific point on the reference plane determined by the third computing part; a fifth computing part which determines a position vector of an image of the region-in-object on the reference plane; and a sixth computing part which determines a position vector of the region-in-object based on the location of the X-ray source vector determined by the fourth computing part and the position vector of the image of the region-in-object determined by the fifth computing part, and which decides an orientation of the region-in-object with respect to the location of the image region-in-object.

According to an eleventh aspect of the invention, there is provided a computing device for measuring a region-in-object comprising: an input part which captures a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other; a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient; a second computing part which determines a projection scaling factor for the image of the object surface frame based on the size of a predetermined pattern on a plane of the object surface frame and the size of an image of a predetermined pattern on the reference plane; a third computing part which determines a position vector of a specific point on the plane of the object surface frame and a position vector of an image of the specific point on the reference plane; a fourth computing part which determines a location of an X-ray source vector based on the projection scaling factor determined by the second computing part and the position vector of a specific point on the plane of the object surface frame and the position vector of an image of the specific point on the reference plane determined by the third computing part; a fifth computing part which determines a position vector of an image of the region-in-object on the reference plane; and a sixth computing part which determines a position vector of the region-in-object based on the location of the X-ray source vector determined by the fourth computing part and the position vector of the image of the region-in-object determined by the fifth computing part, and which decides an orientation of the region-in-object with respect to the location of the image region-in-object.

According to a twelfth aspect of the invention, there is provided the computing device for measuring a region-in-object as described in any one of the eighth to eleventh inventions, wherein data is used that is imaged using an X-ray camera instead of using an X-ray film.

According to a thirteenth aspect of the invention, there is provided a program which is operable to execute: step A of accepting an input of a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface of the object and a film frame which is closely contacted with an X-ray film, and the two frames being separated from each other; step B of determining a projection scaling factor for an image of the object surface frame based on the size of a predetermined pattern on a plane of the object surface frame and the size of an image of a predetermined pattern in a two-dimensional X-ray image on the reference plane; step C of determining a position vector of a specific point on the plane of the object surface frame and a position vector of an image of a specific point on the plane of the object surface frame in the two-dimensional X-ray image; step D of determining a position vector of an X-ray source based on the projection scaling factor determined at step B and the position vector of the specific point on the plane of the object surface frame and the position vector of the image of the specific point on the plane of the object surface frame determined at step C; step E of determining a position vector of an image of the region-in-object in the two-dimensional X-ray image; and step F of determining a position vector of the region-in-object based on the position vector of the X-ray source determined at step D and the position vector of the image of the region-in-object determined at step E, and determining an orientation of the region-in-object with respect to the image of the region-in-object.

According to a fourteenth aspect of the invention, there is provided a program which is operable to execute: step A of accepting an input of two or more two-dimensional X-ray images obtained by imaging a region-in-object from different directions by means of an X-ray imaging apparatus in a state in which an object surface frame of a reference object is closely contacted with a surface of the object, the reference object having the object surface frame which is closely contacted with the surface of the object and a film frame which is closely contacted with an X-ray film, and the two frames being separated from each other; step B of determining a projection scaling factor for an image of the object surface frame based on the size of a predetermined pattern on a plane of the object surface frame and the size of an image of a predetermined pattern in a two-dimensional X-ray image; step C of determining a position vector of a specific point on the plane of the object surface frame and a position vector of an image of a specific point on the plane of the object surface frame in the two-dimensional X-ray image; step D of determining a position vector of an X-ray source based on the projection scaling factor determined at step B and the position vector of the specific point on the plane of the object surface frame and the position vector of the image of the specific point on the plane of the object surface frame determined at step C; step E of determining a position vector of an image of the region-in-object in the two-dimensional X-ray image; step F of determining a position vector of the region-in-object based on the position vector of the X-ray source determined at step F and the position vector of the image of the region-in-object determined at step E; and step G of deciding a three-dimensional location of the region-in-object based on two or more of position vectors of the region-in-object determined at step F.

According to a fifteenth aspect of the invention, there is provided a program which is operable to execute: step A of accepting an input of a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other; step B of determining a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient; step C of determining a projection scaling factor for the image of the object surface frame based on the size of a predetermined pattern on a plane of the object surface frame and the size of an image of a predetermined pattern on the reference plane; step D of determining a position vector of a specific point on the plane of the object surface frame and a position vector of an image of the specific point on the reference plane; step E of determining a location of an X-ray source vector based on the projection scaling factor determined at step B and the position vector of a specific point on the plane of the object surface frame and the position vector of an image of the specific point on the reference plane determined at step C; step F of determining a position vector of an image of the region-in-object on the reference plane; and step G of determining a position vector of the region-in-object based on the location of the X-ray source vector determined step E and the position vector of the image of the region-in-object determined at step F, and deciding an orientation of the region-in-object with respect to the location of the image region-in-object.

According to a sixteenth aspect of the invention, there is provided a program which is operable to execute: step A of accepting an input of two or more of a two-dimensional X-ray images obtained by imaging a region-in-object from different directions by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other; step B of determining a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient; step C of determining a projection scaling factor for the image of the object surface frame based on the size of a predetermined pattern on a plane of the object surface frame and the size of an image of a predetermined pattern on the reference plane; step D of determining a position vector of a specific point on the plane of the object surface frame and a position vector of an image of a specific point on the reference plane; step E of determining a location of an X-ray source vector based on the projection scaling factor determined at step C and the position vector of a specific point on the plane of the object surface frame and the position vector of an image of the specific point on the reference plane determined at step D; step F of determining a position vector of an image of the region-in-object on the reference plane; step G of determining a position vector of the region-in-object based on the location of the X-ray source vector determined at step F and the position vector of the image of the region-in-object determined at step F; and step H of deciding a three-dimensional location of the region-in-object based on two or more of position vectors of the region-in-object determined at step G.

According to a seventeenth aspect of the invention, there is provides the program as described in any one of thirtieth to sixtieth inventions, wherein data is used that is imaged using an X-ray camera instead of using an X-ray film.

According to an eighteenth aspect of the invention, there is provided a computer readable recording medium on which a program according to any one of the thirtieth to seventieth inventions is recorded.

In accordance with the invention, with the use of a single two-dimensional X-ray photograph and the reference object, the orientation of the particular region inside a body can be accurately determined with respect to the image of the particular region inside the body at low costs as effort required for measurement and an X-ray radiation exposure to a patient are suppressed as much as possible.

In addition, in accordance with the invention, with the use of two or more of the two-dimensional X-ray photographs and the reference object, the three-dimensional location of the particular region inside a body can be determined accurately with respect to the image of the particular region inside the body at low costs as effort required for measurement and an X-ray radiation exposure to a patient are suppressed as much as possible.

Furthermore, in accordance with the invention, with the use of a single two-dimensional X-ray photograph and the reference object, the orientation of the particular region inside an object can be measured simply with respect to the image of the particular region inside a general object, and with the use of two or more of the two-dimensional X-ray photographs and the reference object, the three-dimensional location of the particular region inside an object can be measured simply with respect to the image of the particular region inside the object.

BEST MODE FOR CARRYING OUT THE INVENTION

The present invention has the features as described above. Hereinafter, embodiments thereof will be described.

First, a region-in-object measuring system according to a first embodiment of the present invention will be described. The region-in-object measuring system has a reference object and a computing device, in which a three-dimensional rectangular coordinate system is configured that has a predetermined point of the reference object as an origin point, and the orientation of a particular region inside an object is determined with respect to a reference position of the surface of the object (the location of the image of the particular region in an X-ray image).

Figure 1:
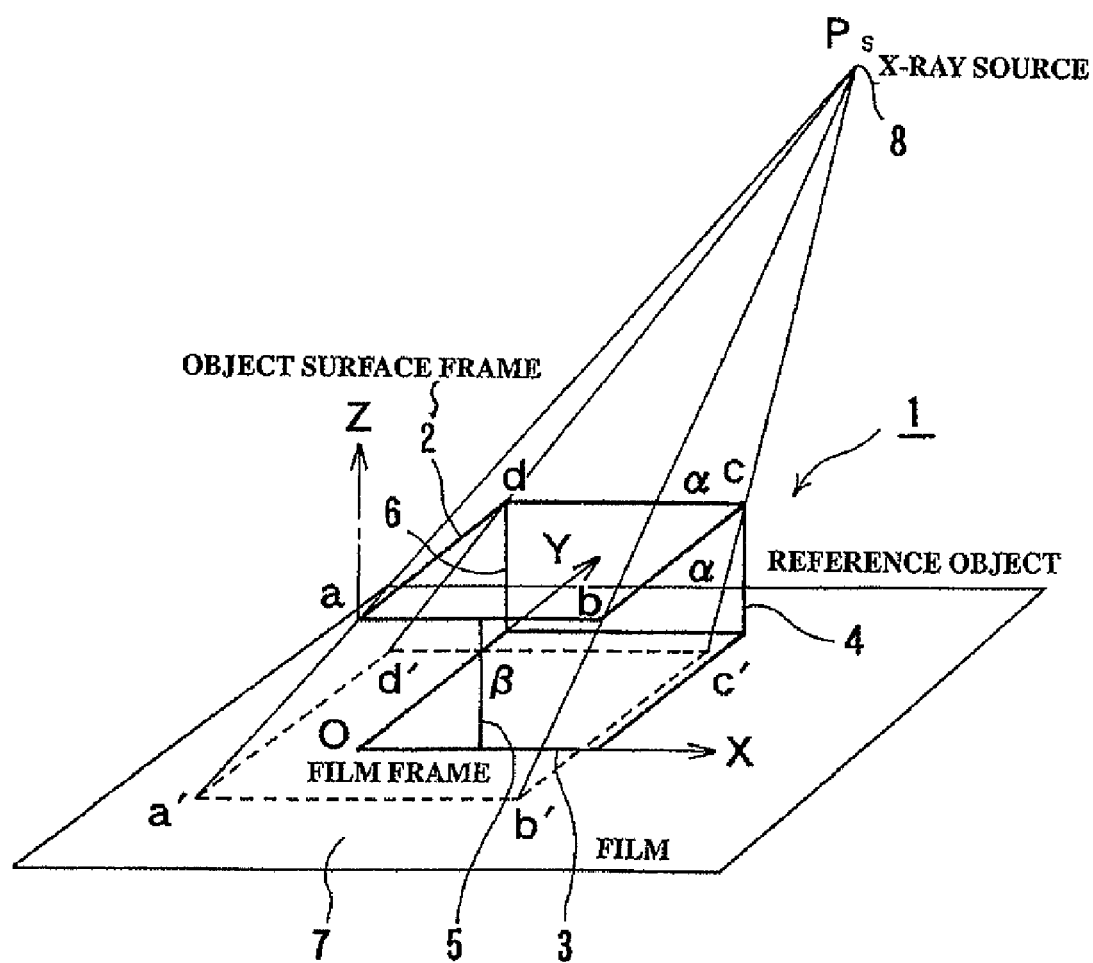
FIG. 1 shows an illustration depicting a reference object, a scheme of X-ray imaging, and a configured three-dimensional space in a region-in-object measuring system according to a first embodiment of the invention.

As shown in FIG. 1, a reference object (1) has two frames (2) and (3) separated from each other. One frame (2) is a frame that is closely contacted with the surface of the object, and the other frame (3) is a frame that is closely contacted with an X-ray film. In the specification of the application, the frame (2) that is closely contacted with the surface of the object is referred to as "an object surface frame", and the frame (3) that is closely contacted with the X-ray film is referred to as "a film frame". In addition, in the case in which a body is a target, "the surface of the object" includes general integuments as well as a mucous membrane inside a mouth in a broad sense. The reference object (1) is supported so that the square object surface frame (2) having a side of length α, for example, is placed as separated from the square film frame (3) in the same size by a fixed distance β in parallel and they are supported by support members (4), (5), and (6). For the materials to configure the object surface frame (2), the film frame (3), and the support members (4), (5), and (6), for example, a metal wiring such as iron and steel may be used. As an example, in order to measure the mental foramen, α can be 2 cm, and β can be 1 cm. Naturally, the values of α and β may be set properly depending on the size of the measurement target. In addition, the shape of the frame of the reference object (1) is not necessarily a square in principles, and may be a proper shape such as a rectangle. However, a square frame is particularly easily handled and advantageous. In addition, in the drawing, (7) denotes an X-ray film, and (8) denotes an X-ray source.

Figure 2:
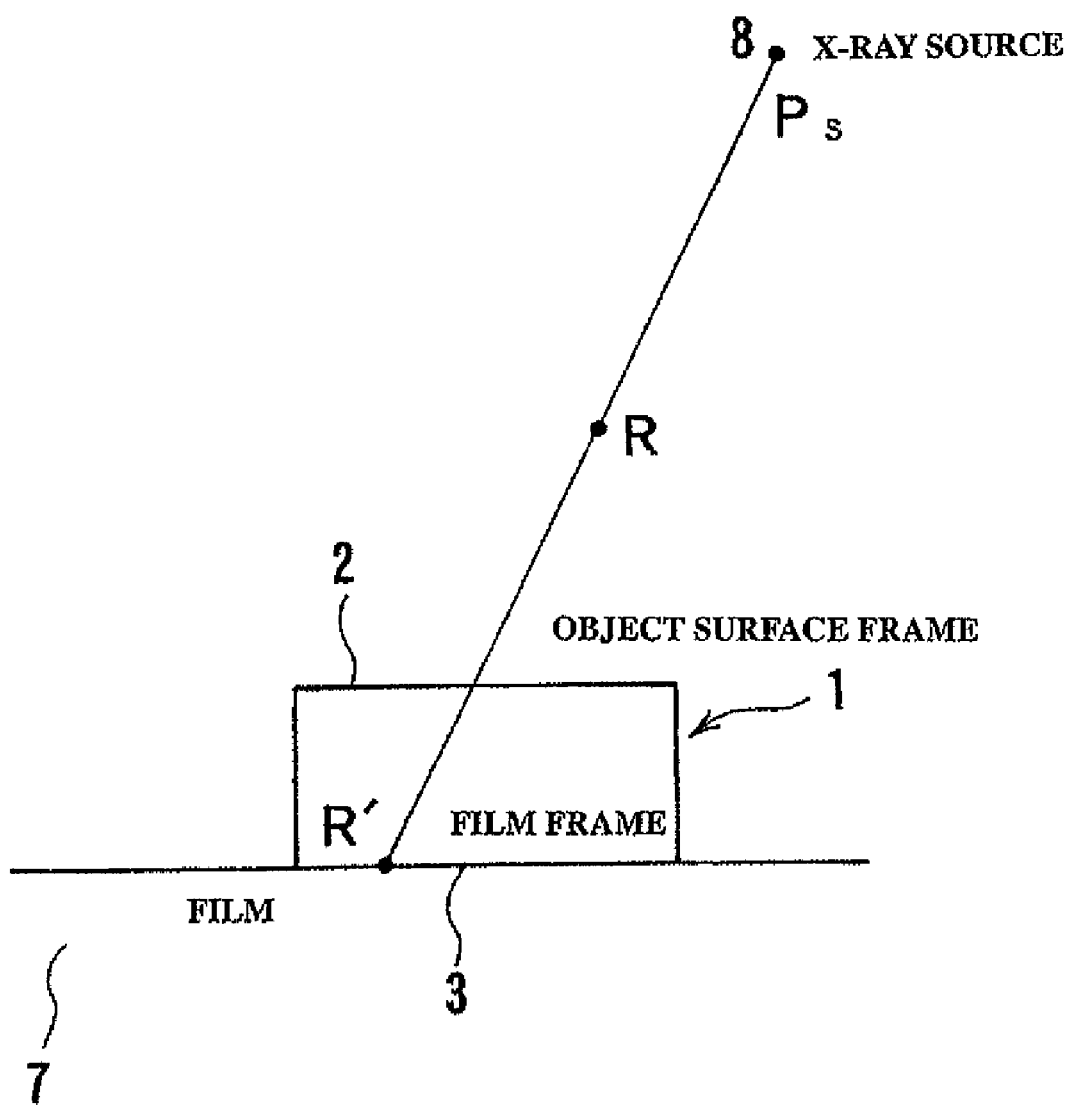
FIG. 2 shows a side view depicting the relation between an object surface frame and a film frame of the reference object, an X-ray film, an X-ray source, a particular region R inside an object, and an image R' of the particular region R on the X-ray film.

FIG. 2 shows a side view depicting the relation between the object surface frame (2) and the film frame (3) of the reference object (1), the X-ray film (7), the X-ray source (8), a particular region R inside an object, and an image R' of the particular region R on the X-ray film (7).

Figure 3:
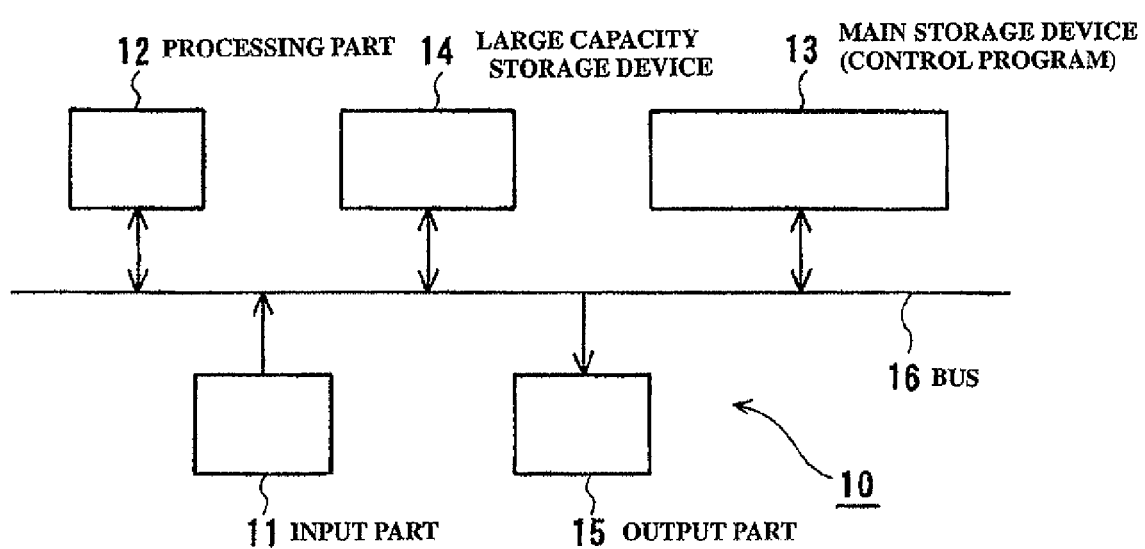
FIG. 3 shows a block diagram depicting the schematic hardware configuration of a computing device of the region-in-object measuring system according to the first embodiment of the invention.

Next, a computing device will be described. FIG. 3 shows a block diagram depicting the schematic hardware configuration of the computing device. The computing device (10) has an input part (11), a processing part (12), a main storage device (13), a large capacity storage device (14), and an output part (15), and they are connected to each other through a bus (16).

The input part (11) captures a two-dimensional X-ray image obtained by taking a particular region inside an object by means of an X-ray imaging apparatus in the state in which the object surface frame (2) of the reference object (1) is closely contacted with the surface of the object. In the embodiment, it is supposed that image information of a single X-ray photograph is captured.

Figure 4:
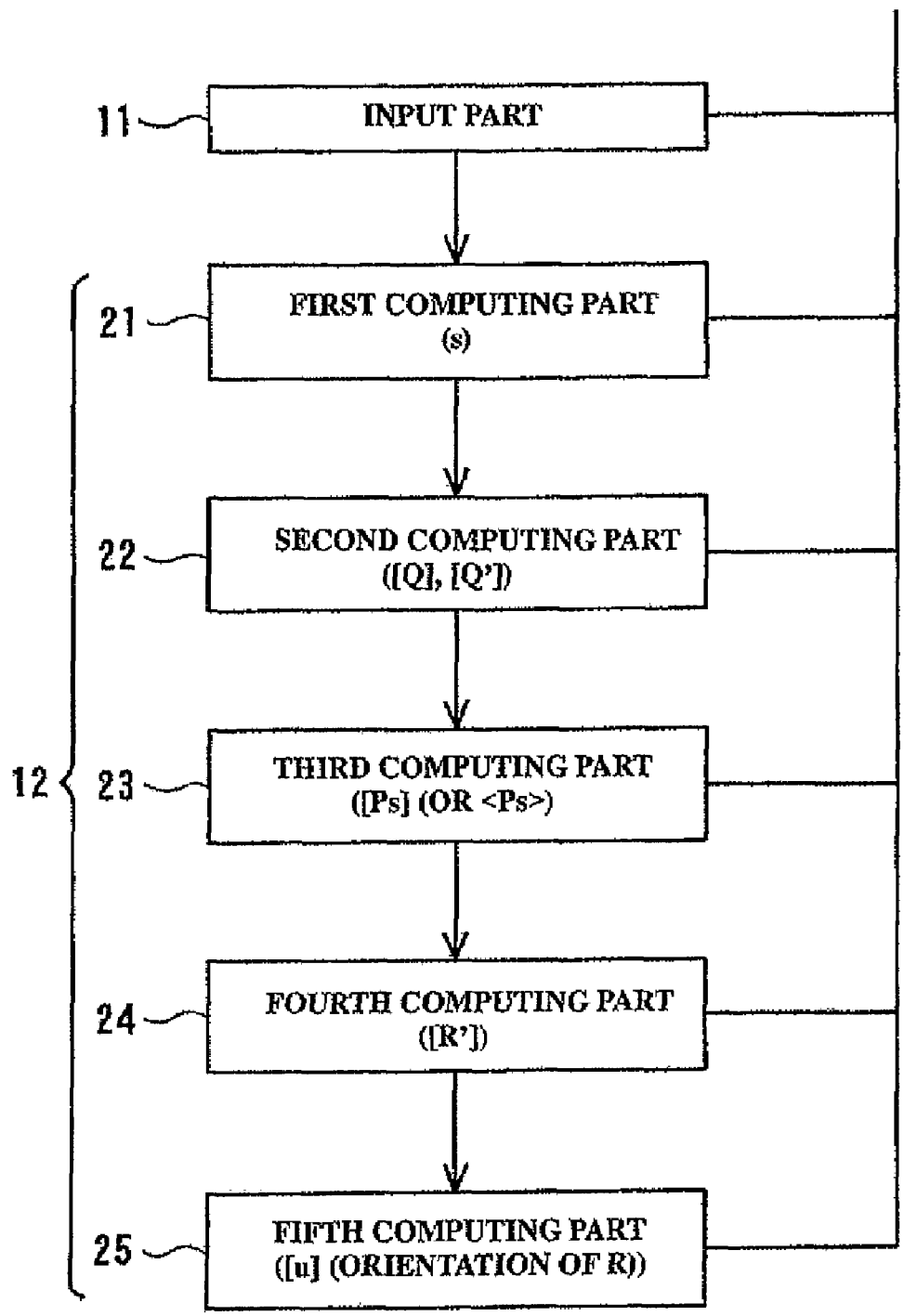
FIG. 4 shows a block diagram depicting the configuration of a processing part of the computing device.

As shown in FIG. 4, the processing part (12) has a first computing part (21), a second computing part (22), a third computing part (23), a fourth computing part (24), and a fifth computing part (25).

The first computing part (21) determines a projection scaling factor (linear scaling factor) s of an image of the object surface frame (2) based on the size of a predetermined pattern on the plane of the object surface frame (2) and the size of an image of the predetermined pattern in a two-dimensional X-ray image. A predetermined pattern may be a linear line, or may be a two-dimensional pattern.

Figure 5:
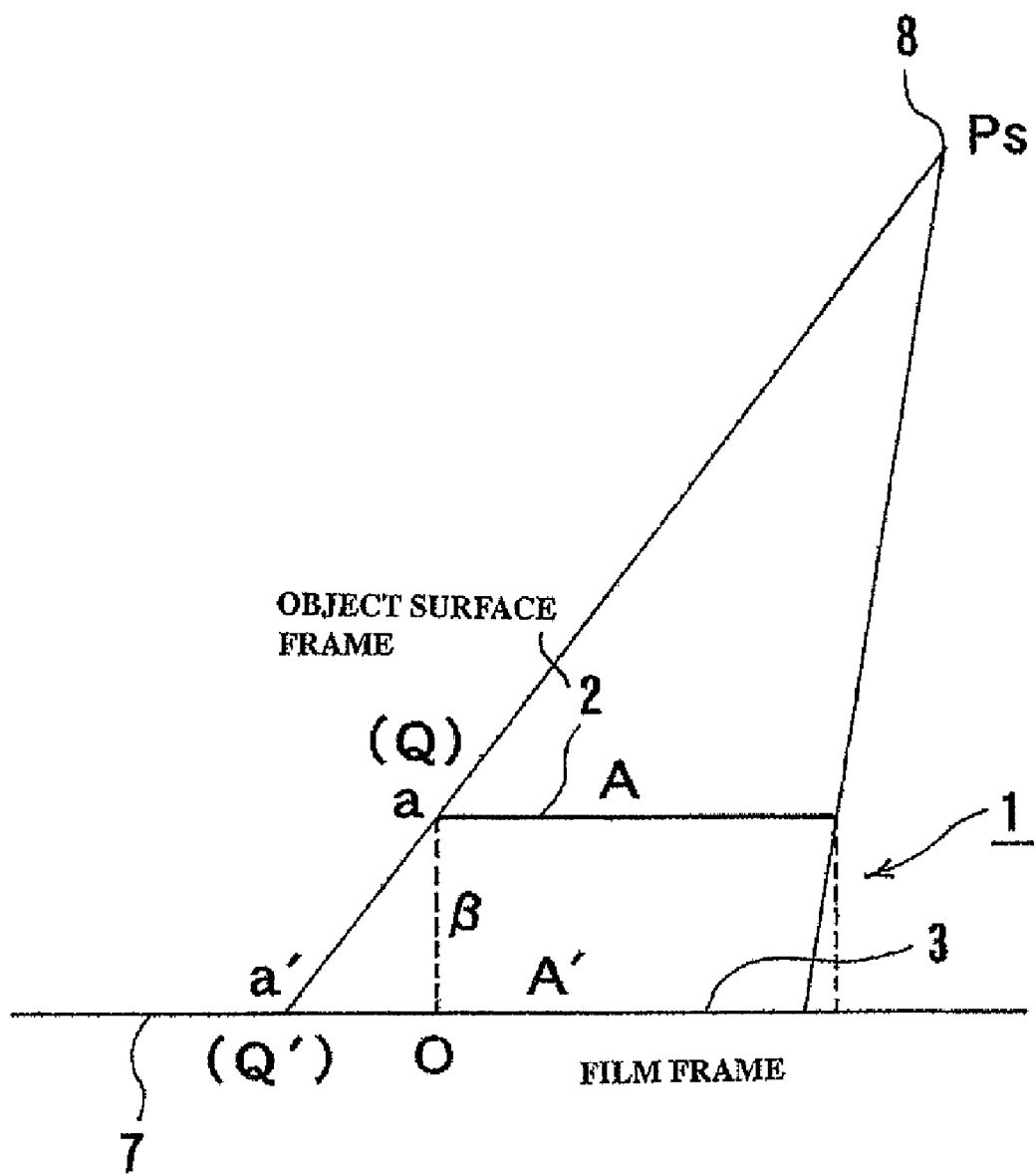
FIG. 5 shows an illustration for determining a projection scaling factor s of the image of the object surface frame of the reference object and the location of the X-ray source.

The second computing part (22) determines a specific point on the plane of the object surface frame (2), for example, a position vector [Q] for Q in FIG. 5 (in the specification of the application, the vector is denoted by [ ], and it is the same below) and a position vector [Q'] for an image Q' of the specific point Q on the plane of the object surface frame (2) in the two-dimensional X-ray image. The position vector [Q] may be set in advance.

The third computing part (23) determines a position vector [Ps] of the X-ray source (8) (or its homogeneous coordinate representation <Ps>) based on the projection scaling factor s determined by the first computing part (21), and the position vector [Q] of the specific point Q on the plane of the object surface frame (2) and the position vector [Q'] of the image Q' of the specific point Q on the plane of the object surface frame (2) determined by the second computing part (21).

The fourth computing part (24) determines a position vector [R'] of an image R' of a region-in-object R in the two-dimensional X-ray image.

The fifth computing part (25) determines an orientation vector [u] of the region-in-object R based on the position vector [Ps] of the X-ray source (8) (or <Ps>) determined by the third computing part (23), and the position vector [R'] of the image R' of the region-in-object determined by the fourth computing part (24), and determines the orientation of the region-in-object R with respect to the image R' of the region-in-object.

The main storage device (13) has a control program for the computing device (10), which controls the operations of the individual parts based on the control program.

The large capacity storage device (14) is a memory device that can store the results computed by the individual parts, for example, in addition to X-ray image data captured by the input part (10), for which an internal storage device such as a hard disk drive, an optical-magnetic disk drive, and a DVD drive, or an external storage device may be used.

The output part (15) is a unit that outputs the results computed by the computing device (10), for which an image output unit like a display or a unit that outputs prints such as a printer may be used.

The functionalities of the individual parts of the computing device (10) may be implemented by a computer or various devices connected thereto (including attached units such as a keyboard, a display, etc.).

Next, an imaging method of an X-ray photograph for use in the region-in-object measuring system according to the embodiment will be described. As shown in FIGS. 1, 2 and 5, the object surface frame (2) of the reference object (1) is closely contacted with the surface of the object, and X-rays are applied from the X-ray source (8) of the X-ray imaging apparatus for shooting in the state in which the X-ray film (7) is closely contacted with the film frame (3), where the individual vertices of the object surface frame (2) are a, b, c, and d, and the image on the X-ray film (7) is a', b', c', and d'.

In the region-in-object measuring system according to the embodiment, a single two-dimensional X-ray photographic image taken by the method described above is captured in the input part (11) of the computing device (10), it is stored in the large capacity storage device (14), the image data is used to perform the computing processes by the individual computing parts based on the principles shown below, whereby the orientation of the particular region inside an object is determined.

When an X-ray photograph is taken by the method described above, the film frame (3) of the reference object (1) is taken in the same size and shape as a real object, but the object surface frame (2) is taken at the different location and in the different size depending on the location Ps of the X-ray source (8). However, since the X-ray film (7) and the object surface frame (2) are in parallel with each other, the shape of the image taken on the X-ray film (7) is similar to the shape of the object surface frame (2), resulting in a square. Accordingly, the location Ps of the X-ray source (8) can be determined from the location and the scaling factor for the square of the image taken on the X-ray film (7).

For more detailed description, first, the coordinate system to specify a three-dimensional location is introduced as below. As shown in FIG. 1, one of vertices of the film frame (3) is taken as an origin point O, and two sides connected thereto are an X-axis and a Y-axis. A Z-axis is taken so that it is orthogonal to these axes and faces to the object surface frame (2). Then, three-dimensional coordinates with right-handed X, Y and Z-axes are configured. The X-ray film (7) has a front surface on the reference object (1) side, and uses a two-dimensional coordinate system configured of the X-axis and Y-axis for specifying the location on the X-ray film (7).

Here, a plane (the plane $Z=\beta$) including the object surface frame (2) and a plane (XY plane) including the film frame (3) are considered. Since the plane of the object surface frame (2) and the plane of the film frame (3) are in parallel with each other, for example, a two-dimensional pattern on the plane of the object surface frame (2) is taken in a similar shape on the X-ray film (7) regardless of the location Ps of the X-ray source (8). As shown in FIG. 5, a similar scaling factor s is s=A'/A, where the original size of a side of this pattern is A, and the size on the X-ray film (7) is A'. On the other hand, suppose that a certain point Q on the plane of the object surface frame (2) is taken on a point Q' on the X-ray film (7), the location Ps of the X-ray source (8) is on the straight line connecting Q' to Q. In addition, the ratio of the lengths of the straight line Q'Q and the straight line Q'Ps is s:(s−1) due to the similar relation. Thus, the location Ps of the X-ray source (8) is given by Equation (1). Here, [Ps], [Q], and [Q'] are the position vectors of Ps, Q, and Q', respectively.

$$[Ps] = \frac{s}{s-1}([Q]-[Q']) + [Q'] = \frac{s[Q]-[Q']}{s-1} \quad (1)$$

Theoretically, Equation (1) is true unless otherwise the X-ray source (8) is infinity. However, in real computation, it is unstable in the case in which the X-ray source (8) is located at a far place and the scaling factor s is close to 1. In order to avoid this problem, the following is obtained when homogeneous coordinates <Ps> are used for expression of the location of the X-ray source (8).

$$<Ps> = \begin{pmatrix} s[Q]-[Q'] \\ s-1 \end{pmatrix} \quad (2)$$

In the expression of Equation (2), even the X-ray source (8) that is theoretical infinity can be expressed correctly.

For specific computation using the reference object (1), Q is taken at a vertex a of the object surface frame (2) is taken that is connected to the origin point O and Q' is taken on an image a', and then the position vectors thereof are as expressed in Equation (3), where the location of a' on the XY plane is ($X_{a'}$, $Y_{a'}$).

$$[Q] = \begin{pmatrix} 0 \\ 0 \\ \beta \end{pmatrix}, [Q'] = \begin{pmatrix} X_{a'} \\ Y_{a'} \\ 0 \end{pmatrix} \quad (3)$$

When they are substituted in Equation (2), <Ps> is computed as below.

$$<Ps> = \begin{pmatrix} -X_{a'} \\ -Y_{a'} \\ s\beta \\ s-1 \end{pmatrix} \quad (4)$$

The X and Y-axes are given by the film frame (3) taken on the X-ray image. With reference to this, it is sufficient to measure the location of the image of the object surface frame (2) and the scaling factor. In practice, it is easier to see the locations of the individual sides of the object surface frame (2). However, since there is measurement error, the shape of the image of the object surface frame (2) configured of the locations of the individual sides measured is not always a square. Then, in the embodiment, the measured value is corrected as below to improve accuracy so that the shape of the image of the object surface frame (2) is a square.

In the image of the object surface frame (2) taken on the X-ray film (7), the X-coordinate of a side a'd' in FIG. 1 is $X_1$, the X-coordinate of a side b'c' is $X_2$, the Y-coordinate of a side a'b' is $Y_1$, and the Y-coordinate of a side d'c' is $Y_2$. In order that the image of the object surface frame (2) is a squire, the following equation has to be held.

$$X_2 - X_1 = Y_2 - Y_1 \quad (5)$$

However, the actual measured values do not always satisfy Equation (5) due to error. Then, an optimum value is determined in the sense of least square error. To this end, the following amount is minimized under the condition of Equation (5).

$$D_v^2 = (X_1 - X_1^*)^2 + (Y_1 - Y_1^*)^2 + (X_2 - X_2^*)^2 + (Y_2 - Y_2^*)^2 \quad (6)$$

An asterisk on the shoulder in Equation (6) expresses an actual measured value. Lagrange's method of undetermined multipliers is used for computation, and then the coordinate values of the individual sides are as follows.

$$X_1 = X_1^* - \delta, \ X_2 = X_2^* + \delta, \ Y_1 = Y_1^* + \delta, \ Y_2 = Y_2^* - \delta \quad (7)$$

Where, $\delta$ is Equation (8).

$$\delta = \frac{1}{4}((Y_2^* - Y_1^*) - (X_2^* - X_1^*)) \quad (8)$$

The scaling factor s and the location of $a'(X_{a'}, Y_{a'})$ are computed as follows.

$$s = \frac{X_2 - X_1}{\alpha}, \ X_{a'} = X_1, \ Y_{a'} = Y_1 \quad (9)$$

As described above, the location of the X-ray source (8) Ps can be computed from the coordinate values of the individual sides of the object surface frame (2) in the X-ray image. As shown in FIG. 2, the target portion to determine the location is on the straight line connecting the location of R' of the image on the X-ray film (7) to the location Ps of the X-ray source (8). Therefore, since the orientation of the target portion R is known with reference to the reference frame configured on the reference object (1), the orientation of the target portion can be determined. The detail is as follows.

Suppose that the target portion to determine the location is R, a point on the X-ray image is R', and the position vectors thereof are [R], and [R']. [R'] is as follows, where the X and Y-coordinate values of R' measured from the X-ray image are $X_{R'}, Y_{R'}$.

$$[R'] = \begin{pmatrix} X_{R'} \\ Y_{R'} \\ 0 \end{pmatrix} \quad (10)$$

Since the target portion R is on the straight line connecting the image R' to the location Ps of the X-ray source (8), [R] is expressed as follows, where t is the parameter of a proper value and Equation (1) is used for [Ps].

$$[R] = t([Ps] - [R']) + [R'] = t\left(\frac{s[Q] - [Q']}{s - 1} - [R']\right) + [R'] \quad (11)$$

However, Equation (11) causes a problem in practical computation in the case in which the difference is close to one, which is modified as follows.

$$[R] = q[u] + [R'] \quad (12)$$

Where, [u] and q are as follows.

$$[u] = s[Q] + (s - 1)[R'] - [Q] \quad (13)$$

$$q = \frac{t}{s - 1} \quad (14)$$

Equation (12) expresses that the target portion R exists in the orientation indicated by the vector [u] of Equation (13) with reference to the location of R'. In the case in which only the orientation of the target portion is desired to know, the orientation can be determined by the steps described above.

Figure 6:
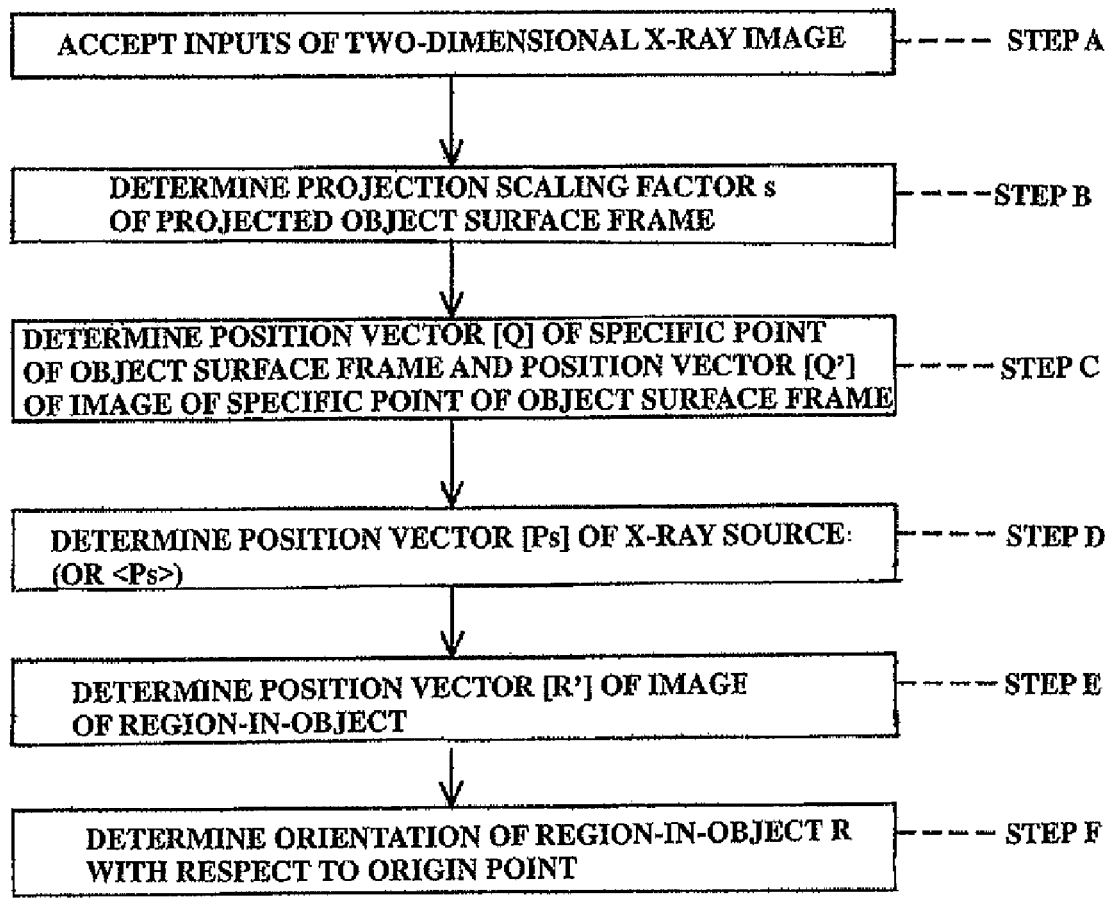
FIG. 6 shows a flow chart depicting the steps of a computing process performed by the processing part of the computing device shown in FIG. 4.

As described above, the computation to determine s is performed by the first computing part (21), the computation to determine [Q] and [Q'] is performed by the second computing part (22), the computation to determine [Ps] (or <Ps>) is performed by the third computing part (23), the computation to determine [R'] is performed by the fourth computing part (24), the computation to determine [u], that is, the orientation of the target portion R is determined by the fifth computing part (25), and then the orientation of the target portion is determined. A flow of the computing processes is shown in FIG. 6.

Next, a region-in-object measuring system according to a second embodiment of the present invention will be described. As similar to the first embodiment, the region-in-object measuring system has a reference object and a computing device, in which a three-dimensional rectangular coordinate system is configured that has a predetermined point of the reference object as an origin point and a three-dimensional location of a particular region inside the object is determined.

In the embodiment, for the reference object, the same ones used in the first embodiment can be used. In addition, in the second embodiment, the same numerals and signs are assigned to the similar components as those of the first embodiment other than the configuration of the processing part.

Figure 7:
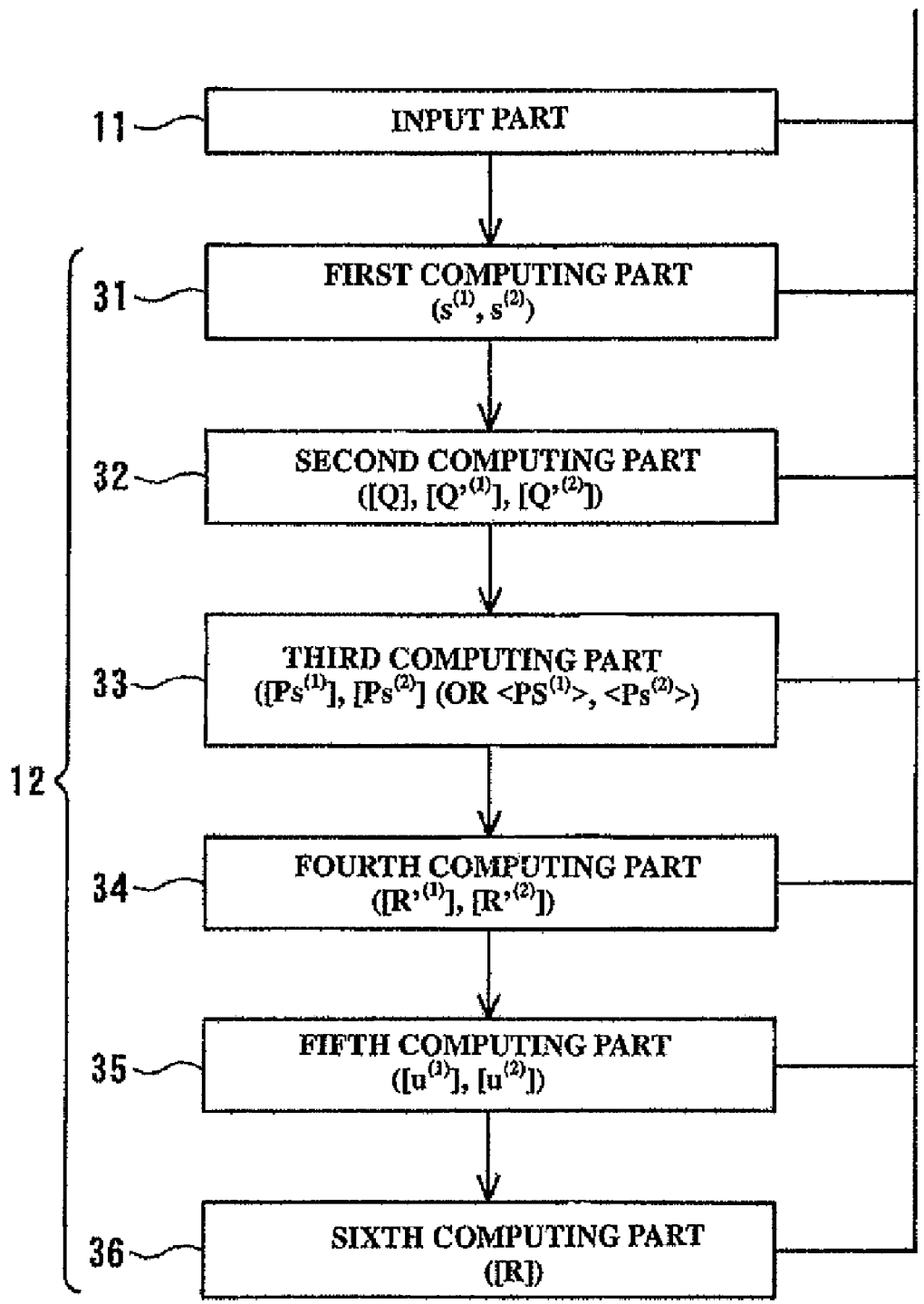
FIG. 7 shows a block diagram depicting the configuration of a processing part of a computing device in a region-in-object measuring system according to a second embodiment of the invention.

Although the schematic hardware configuration of the computing device may have the similar configuration as that of the first embodiment, a processing part (12) is configured as shown in FIG. 7.

An input part (11) captures two two-dimensional X-ray images obtained by taking a region-in-object from two different directions in the state in which an object surface frame (2) of a reference object (1) is closely contacted with the surface of an object. In the embodiment, it is supposed that image information of two X-ray photographs is inputted. In addition, hereinafter, since two X-ray images are used for computation, in order to distinguish the values of the individual variables used above in X-ray images, a bracketed numeral is denoted on the shoulder of the individual variables.

As shown in FIG. 7, the processing part (12) has a first computing part (31), a second computing part (32), a third computing part (33), a fourth computing part (34), a fifth computing part (35), and a sixth computing part (36).

The first computing part (31) determines the projection scaling factors $s^{(1)}$ and $S^{(2)}$ of the projected object surface frame (2) based on the size of a predetermined pattern on the plane of the object surface frame (2) and the size of an image of a predetermined pattern in the two-dimensional X-ray image with respect to the two X-ray images. A predetermined pattern may be a linear line, or may be a two-dimensional pattern.

The second computing part (32) determines a position vector [Q] of a specific point Q on the plane of the object surface frame (2) and position vectors $[Q'^{(1)}]$ and $[Q'^{(2)}]$ of images $Q'^{(1)}$ and $Q'^{(2)}$ of the specific point Q on the plane of the object surface frame (2) in the two-dimensional X-ray images with respect to the two X-ray images. The position vector [Q] may be set in advance.

The third computing part (33) determines position vectors $[Ps^{(1)}]$ and $[Ps^{(2)}]$ (or $<Ps^{(1)}>$ and $<Ps^{(2)}>$) of an X-ray source (8) based on the projection scaling factors $s^{(1)}$ and $s^{(2)}$ determined by the first computing part (31), and the position vector [Q] of the specific point Q on the plane of the object surface frame (2) and the position vectors $[Q'^{(1)}]$ and $[Q'^{(2)}]$ of the images $Q'^{(1)}$ and $Q'^{(2)}$ of the specific point Q on the plane of the object surface frame (2) determined by the second computing part (32).

The fourth computing part (34) determines position vectors $[R'^{(1)}]$ and $[R'^{(2)}]$ of images $R'^{(1)}$ and $R'^{(2)}$ of a region-in-object R in a two-dimensional X-ray image.

The fifth computing part (35) determines orientation vectors $[u^{(1)}]$ and $[u^{(2)}]$ of the region-in-object R based on the position vectors $[Ps^{(1)}]$ and $[Ps^{(2)}]$ (or $<Ps^{(1)}>$ and $<Ps^{(2)}>$) of the X-ray source (8) determined by the third computing part (33) and the position vectors $[R'^{(1)}]$ and $[R'^{(2)}]$ of the images $R'^{(1)}$ and $R'^{(2)}$ of the region-in-object determined by the fourth computing part (34).

The computation scheme performed by the first to fifth computing parts (31) to (35) described above is basically the same as the computation scheme performed by the first to fifth computing parts (21) to (25) of the first embodiment.

The sixth computing part (36) determines a intersection point based on the orientation vectors $[u^{(1)}]$ and $[u^{(2)}]$ of the region-in-object R determined by the fifth computing part (35), and determines the point as a three-dimensional location of the region-in-object.

When Equation (12) discussed in the first embodiment is applied to two X-ray images, an equation below is obtained.

$$[R^{(1)}] = q^{(1)}[u^{(1)}] + [R'^{(1)}] \quad (15)$$

$$[R^{(2)}] = q^{(2)}[u^{(2)}] + [R'^{(2)}] \quad (16)$$

$[R^{(1)}]$ and $[R^{(2)}]$ in Equation (15) and Equation (16) express points on two straight lines computed from the two X-ray images, and such points are determined that become closest. To this end, it is sufficient to compute $q^{(1)}$ and $q^{(2)}$ that $D_R$ in the following equation is smallest.

$$D_R^2 = \|[R^{(1)}] - [R^{(2)}]\|^2 = ([R^{(1)}] - [R^{(2)}])^T([R^{(1)}] - [R^{(2)}]) \quad (17)$$

Equation (17) is differentiated for $q^{(1)}$ and $q^{(2)}$, and then the following equation is obtained.

$$\frac{\partial D_R^2}{\partial q^{(1)}} = \quad (18)$$
$$2q^{(1)}[u^{(1)}]^T[u^{(1)}] - 2q^{(2)}[u^{(1)}]^T[u^{(2)}] + 2[u^{(1)}]^T[R'^{(1)}] - 2[u]^{(1)}[R'^{(2)}]$$

$$\frac{\partial D_R^2}{\partial q^{(2)}} = \quad (19)$$
$$2q^{(2)}[u^{(2)}]^T[u^{(2)}] - 2q^{(1)}[u^{(1)}]^T[u^{(2)}] + 2[u^{(2)}]^T[R'^{(1)}] - 2[u]^{(2)}[R'^{(2)}]$$

They are taken as 0 to form in a matrix, and then the following equation is obtained.

$$\begin{pmatrix} q^{(1)} \\ q^{(2)} \end{pmatrix} = \begin{pmatrix} [u^{(1)}]^T[u^{(1)}] & -[u^{(1)}]^T[u^{(2)}] \\ -[u^{(2)}][u^{(1)}] & [u^{(2)}]^T[u^{(2)}] \end{pmatrix}^{-1} \begin{pmatrix} [u^{(1)}]^T([R'^{(2)}] - [R'^{(1)}]) \\ [u^{(2)}]^T([R'^{(1)}] - [R'^{(2)}]) \end{pmatrix} \quad (20)$$

$q^{(1)}$ and $q^{(2)}$ in Equation (20) are substituted in Equation (15) and Equation (16), respectively. From the result, the target position vector [R] is computed as follows.

$$[R] = \frac{[R^{(1)}] + [R^{(2)}]}{2} \quad (21)$$

Figure 8:
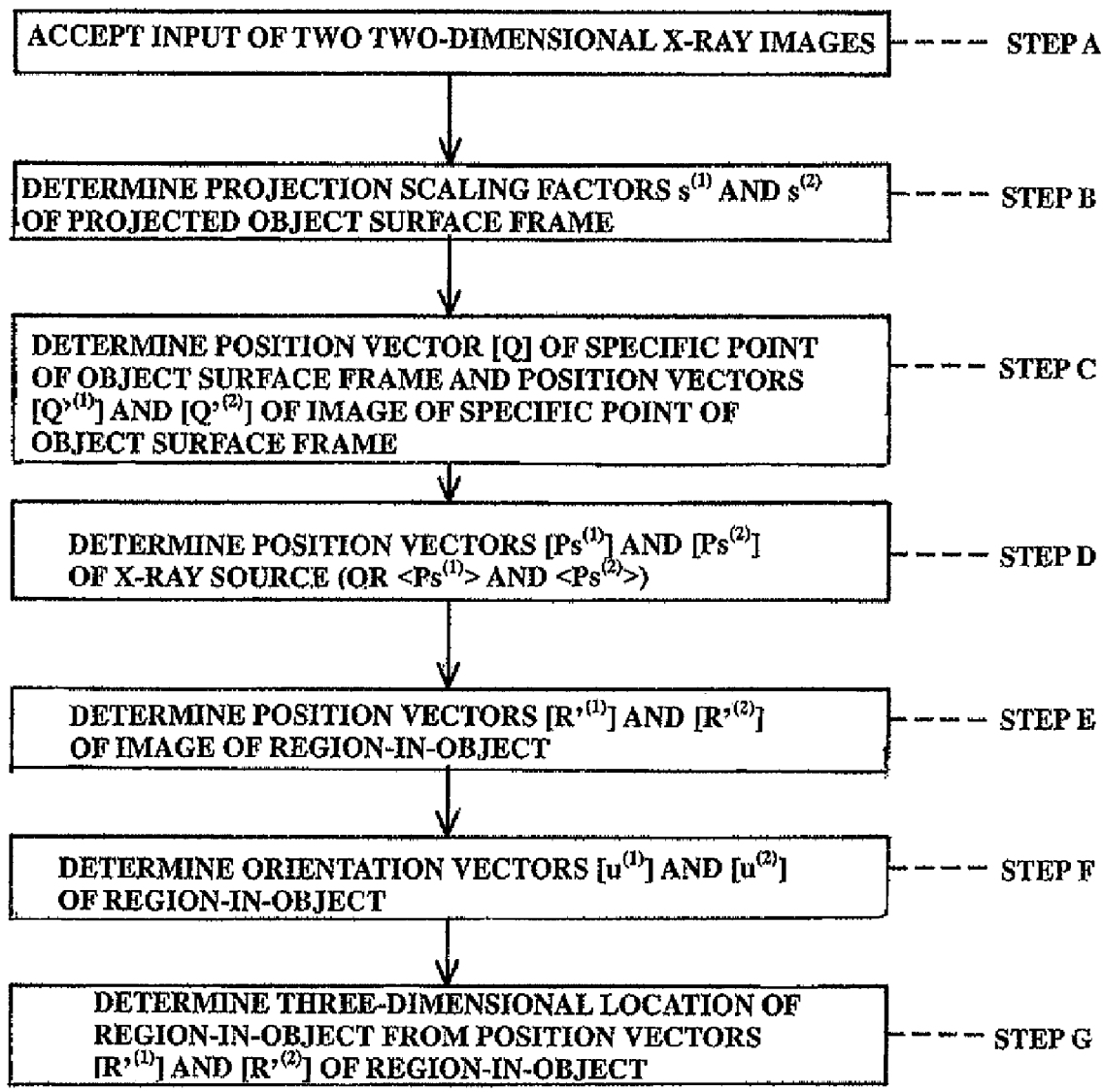
FIG. 8 shows a flow chart depicting the steps of a computing process performed by the processing part of the computing device shown in FIG. 7.

As described above, the location of the region-in-object R is determined. A flow of the computing processes is shown in FIG. 8.

As described above, the second embodiment has been described in which a particular region inside an object is determined by two X-ray photographs. In accordance with the present invention, a particular region inside an object can be determined by three or more of X-ray photographs, and in that case, the accuracy is more improved.

For example, the case is considered in which three X-ray photographs are obtained. Pairs formed of these photographs are three pairs, (photo 1, photo 2), (photo 2, photo 3), and (photo 3, photo 1). Suppose the target locations computed from the three pairs are $[R^{(12)}]$, $[R^{(23)}]$, and $[R^{(31)}]$. As expressed by the following equation, when they are averaged to be a target location [R], more accurate measurement can be implemented.

$$[R] = \frac{1}{3}([R^{(12)}] + [R^{(23)}] + [R^{(31)}]) \quad (22)$$

Next, third and fourth embodiments according to the application will be described.

In the first embodiment and the second embodiment, the X-ray film is placed as closely contacted with one of frames (film frame) of the reference object for shooting. In accordance with the present invention, the X-ray film is not closely contacted with the frame (film frame), it is located at a free location to take the target portion, and the orientation of the region-in-object can be determined with respect to the location of the image of the region-in-object. The third and fourth embodiments determine the orientation of the region-in-object with respect to the location of the image the region-in-object based on the image that is taken as the X-ray film is placed at a free location in the first and second embodiments.

In the third and fourth embodiments, a film frame configuring a reference object is referred to as a "film location reference frame". The structure, material and so on of the film location reference frame are the same as those of the film frame in the first second embodiments.

The geometrical relation between an image taken as the X-ray film is placed at a free location and an image taken as the X-ray film is closely contacted with the film location reference frame of the reference object is related by two-dimensional projection transformation. Suppose that the coefficient of this transformation is determined from the shape of the reference object taken on the X-ray photograph, and the determined transformation coefficient is used to transform the location of the image on the X-ray photograph for transformation. Then, the image can be transformed into an image that the X-ray film is placed as closely contacted with the film location reference frame of the reference object.

Figure 9:
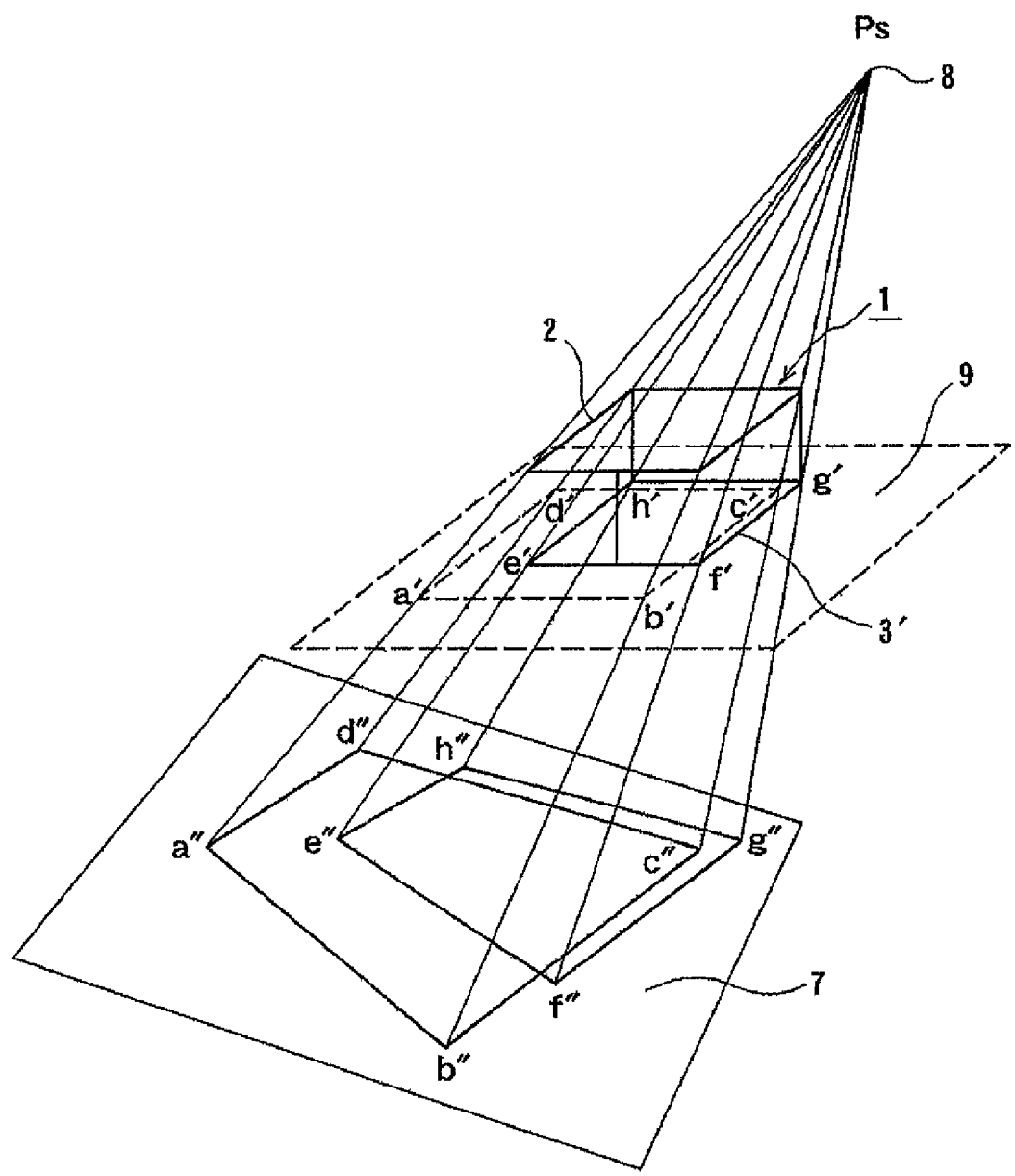
FIG. 9 shows a diagram depicting the relation between an X-ray source, a reference object, an X-ray film, and a reference plane where the X-ray film is placed as closely contacted with the film location reference frame of the reference object.
Figure 10:
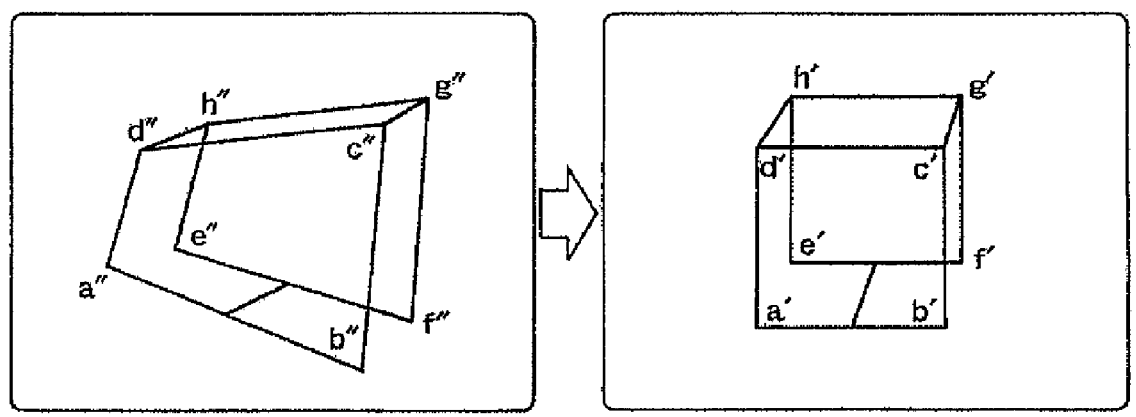
FIG. 10 shows a conceptual diagram depicting transformation of an image in accordance with two-dimensional projection transformation.

FIG. 9 shows the relation between an X-ray source Ps (8), a reference object (1), an X-ray film (7), and a reference plane (9) where the X-ray film (7) is placed as closely contacted with a film location reference frame (3') of the reference object (1). In addition, FIG. 10 shows a conceptual diagram depicting transformation of an image in accordance with two-dimensional projection transformation.

Suppose that four vertices of an image on the reference plane (9) of the film location reference frame (3') of the reference object (1) are points e', f', g', and h', and four vertices of the corresponding image on the X-ray film (7) are points e", f", g", and h".

The two-dimensional projection transformation in which a point (x, y) on the two-dimensional plane is transformed into a point (u, v) on another two-dimensional plane is expressed by the following equation where the coefficient is $a_{ij}$.

$$u = \frac{a_{11}x + a_{12}y + a_{13}}{a_{31}x + a_{32}y + 1} \quad (23)$$

$$v = \frac{a_{21}x + a_{22}y + a_{23}}{a_{31}x + a_{32}y + 1} \quad (24)$$

The coefficient $a_{ij}$ of two-dimensional projection transformation is uniquely determined when the correspondence of four vertices on the image is known. As shown in FIGS. 9 and 10, suppose the location of the image of the individual vertices of the film location reference frame (3') of the reference object (1) is point e"=$(x_1, y_1)$, f"=$(x_2, y_2)$, g"=$(X_3, y_3)$, and h"=$(x_4, y_4)$. Suppose the location to be taken is point e'=$(u_1, v_1)$, f'=$(u_2, v_2)$, g'=$(u_3, v_3)$, and h'=$(x_4, y_4)$, the vertices thereof are $(u_1, v_1)$=$(0, 0)$, $(u_2, v_2)$=$(\alpha, 0)$, $(u_3, v_3)$=$(0, \alpha)$, $(x_4, y_4)$=$(\alpha, \alpha)$, if the X-ray film (7) was closely contacted with the film location reference frame (3'). From these values, the coefficient $a_{ij}$ for two-dimensional projection transformation is determined.

Suppose point $(x_1, y_1)$ is mapped to $(u_1, v_1)$ for the subscript i=1, 2, 3, and 4, the relation below should be held for i by Equation (23) and Equation (24).

$$a_{11}x_i + a_{12}y_i + a_{13} - a_{31}u_ix_i - a_{32}u_iy_1 = u_i \quad (25)$$

$$a_{21}x_i + a_{22}y_i + a_{23} - a_{31}v_ix_i - a_{32}v_iy_1 = v_i \quad (26)$$

When they are expressed using a matrix, the following equation is held.

$$A = \begin{pmatrix} x_1 & y_1 & 1 & 0 & 0 & 0 & -u_1x_1 & -u_1y_1 \\ 0 & 0 & 0 & x_1 & y_1 & 1 & -v_1x_1 & -v_1y_1 \\ x_2 & y_2 & 1 & 0 & 0 & 0 & -u_2x_2 & -u_2y_2 \\ 0 & 0 & 0 & x_2 & y_2 & 1 & -v_2x_2 & -v_2y_2 \\ x_3 & y_3 & 1 & 0 & 0 & 0 & -u_3x_3 & -u_3y_3 \\ 0 & 0 & 0 & x_3 & y_3 & 1 & -v_3x_3 & -v_3y_3 \\ x_4 & y_4 & 1 & 0 & 0 & 0 & -u_4x_4 & -u_4y_4 \\ 0 & 0 & 0 & x_4 & y_4 & 1 & -v_4x_4 & -v_4y_4 \end{pmatrix},$$

$$[a] = \begin{pmatrix} a_{11} \\ a_{12} \\ a_{13} \\ a_{21} \\ a_{22} \\ a_{23} \\ a_{31} \\ a_{32} \end{pmatrix}, [u] = \begin{pmatrix} u_1 \\ v_1 \\ u_2 \\ v_2 \\ u_3 \\ v_3 \\ u_4 \\ v_4 \end{pmatrix}$$

Then, the following equation is obtained.

$$A[a] = [u] \quad (28)$$

Accordingly, $$[a] = A^{-1}[u] \quad (29)$$

The vector [a] can be computed from above, and the coefficient $a_{ij}$ for two-dimensional projection transformation is determined from the elements.

From the description above, the points e", f", g", and h" on the X-ray film (7) can be determined. Similarly, the location of the vertices a", b", c" and d" of the image of the object surface frame (2) on the X-ray film (7) and the location of R'$(X_R, Y_R)$ of the image of the target portion on the X-ray film (7) are subjected to two-dimensional projection transformation into the location of the vertices a', b', c', d' of the image on the reference plane (9) and the location of R'$(X_{R'}, Y_{R'})$ of the image of the target portion on the X-ray film (7) using the coefficient. Then, data of an image is obtained that is equivalent to an image taken as the X-ray film (7) is closely contacted with the film location reference frame (3'). The data is used to perform the similar processes as those of the first and second embodiments, whereby the orientation of the region-in-object can be determined with respect to the location of the image the region-in-object based on the image taken as the X-ray film (7) is placed at a free location.

Therefore, in the third and fourth embodiments, the reference object is allowed to be a reference object having two frames, the object surface frame that is closely contacted with the surface of the object and the film location reference frame that is the reference of the location of the X-ray film placed at a free location in the first and second embodiments. The computing parts are provided in which a transformation coefficient is newly determined that the image of the film location reference frame on the X-ray film is subjected to two-dimensional projection transformation into the image of the film location reference frame on the reference plane, the image has to be taken in the state in which the X-ray film is closely contacted with the film location reference frame, and the image of the object surface frame on the two-dimensional X-ray image is subjected to two-dimensional projection transformation into an image of the object surface frame on the reference plane using the transformation coefficient.

According to the third and fourth embodiments, an advantage is provided that the operational performance in taking an X-ray photograph is further improved in addition to the advantages of the first and second embodiments.

In addition, in the description above, the case is described in which the X-ray film is used for imaging. In accordance with the present invention, an X-ray camera may be used as an electronic device having the functionality equal to the X-ray film. In this case, the obtained image is directly captured into a personal computer, for example, for processing, whereby measurement can be further simplified.

In accordance with the invention according to the application, a computer program is provided which executes the individual steps of the computing processes in the first to fourth embodiments (for example, processes in the flows in FIGS. 6 and 8).

In addition, in accordance with the present invention, a recording medium such as a flexible disk, CD, and DVD on which the program is readably stored.

Naturally, the present invention is not limited to the embodiments above, the detail of which may be modified variously.

The invention claimed is:

1. A region-in-object measuring system comprising:
   a reference object having an object surface frame which is closely contacted with a surface of an object and a film frame which is closely contacted with an X-ray film, the two frames being separated from each other; and
   a computing device having:
      an input part which captures a two-dimensional X-ray image obtained by imaging a region-in-object by means of an X-ray imaging apparatus in a state in which the object surface frame of the reference object is closely contacted with the surface of the object;

a first computing part which determines a projection scaling factor for an image of the object surface frame based on the size of a predetermined pattern on a plane of the object surface frame and the size of an image of a predetermined pattern in a two-dimensional X-ray image;

a second computing part which determines a position vector of a specific point on the plane of the object surface frame and a position vector of an image of a specific point on the plane of the object surface frame in the two-dimensional X-ray image;

a third computing part which determines a position vector of an X-ray source based on the projection scaling factor determined by the first computing part and the position vector of the specific point on the plane of the object surface frame and the position vector of the image of the specific point on the plane of the object surface frame determined by the second computing part;

a fourth computing part which determines a position vector of an image of the region-in-object in the two-dimensional X-ray image; and a fifth computing part which determines a position vector of the region-in-object based on the position vector of the X-ray source determined by the third computing part and the position vector of the image of the region-in-object determined by the fourth computing part, and which decides an orientation of the region-in-object with respect to the location of the image region-in-object.

2. A region-in-object measuring system comprising:

a reference object having an object surface frame which is closely contacted with a surface of an object and a film frame which is closely contacted with an X-ray film, the two frames being separated from each other; and a computing device having:

an input part which captures two or more of two-dimensional X-ray images obtained by imaging a region-in-object from different directions by means of an X-ray imaging apparatus in a state in which the object surface frame of the reference object is closely contacted with the surface of the object;

a first computing part which determines a projection scaling factor for an image of the object surface frame based on the size of a predetermined pattern on a plane of the object surface frame and the size of an image of a predetermined pattern in a two-dimensional X-ray image;

a second computing part which determines a position vector of a specific point on the plane of the object surface frame and a position vector of an image of a specific point on the plane of the object surface frame in the two-dimensional X-ray image;

a third computing part which determines a position vector of an X-ray source based on the projection scaling factor determined by the first computing part and the position vector of the specific point on the plane of the object surface frame and the position vector of the image of the, specific point on the plane of the object surface frame determined by the second computing part;

a fourth computing part which determines a position vector of an image of the region-in-object in the two-dimensional X-ray image;

a fifth computing part which determines a position vector of the region-in-object based on the position vector of the X-ray source determined by the third computing part and the position vector of the image of the region-in-object determined by the fourth computing part; and a sixth computing part which decides a three-dimensional location of the region-in-object based on two or more of position vectors of the region-in-object determined by the fifth computing part.

3. A region-in-object measuring system comprising:

a reference object having an object surface frame which is closely contacted with a surface of an object and a film location reference frame which is a reference of an X-ray film placed at a free location, the two frames being separated from each other; and a computing device having:

an input part which captures a two-dimensional X-ray image obtained by imaging a region-in-object by means of an X-ray imaging apparatus in a state in which the object surface frame of the reference object is closely contacted with the surface of the object;

a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient;

a second computing part which determines a projection scaling factor for the image of the object surface frame based on the size of a predetermined pattern on a plane of the object surface frame reference plane and the size of an image of a predetermined pattern on the reference plane;

a third computing part which determines a position vector of a specific point on the plane of the object surface frame and a position vector of the specific point on the reference plane;

a fourth computing part which determines a location of an X-ray source vector based on the projection scaling factor determined by the second computing part and the position vector of a specific point on the plane of the object surface frame and the position vector of an image of the specific point on the reference plane determined by the third computing part;

a fifth computing part which determines a position vector of an image of the region-in-object on the reference plane; and a sixth computing part which determines a position vector of the region-in-object based on the location of the X-ray source vector determined by the fourth computing part and the position vector of the image of the region-in-object determined by the fifth computing part, and which decides an orientation of the region-in-object with respect to the location of the image region-in-object.

4. A region-in-object measuring system comprising:

a reference object having an object surface frame which is closely contacted with a surface of an object and a film location reference frame which is a reference of an X-ray film placed at a free location, the two frames being separated from each other; and a computing device having:

an input part which captures two or more of two-dimensional X-ray images obtained by imaging a region-in-object from different directions by means of an X-ray imaging apparatus in a state in which the object surface frame of the reference object is closely contacted with the surface of the object;

a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient;

a second computing part which determines a projection scaling factor for the image of the object surface frame based on the size of a predetermined pattern on a plane of the object surface frame and the size of an image of a predetermined pattern on the reference plane;

a third computing part which determines a position vector of a specific point on the plane of the object surface frame and a position vector of an image of a specific point on the reference plane;

a fourth computing part which determines a location of an X-ray source vector based on the projection scaling factor determined by the second computing part and the position vector of a specific point on the plane of the object surface frame and the position vector of an image of the specific point on the reference plane determined by the third computing part;

a fifth computing part which determines a position vector of an image of the region-in-object on the reference plane;

a sixth computing part which determines a position vector of the region-in-object based on the location of the X-ray source vector determined by the fourth computing part and the position vector of the image of the region-in-object determined by the fifth computing part; and a seventh computing part which decides a three-dimensional location of the region-in-object based on two or more of position vectors of the region-in- object determined by the sixth computing part.

5. The region-in-object measuring system according to any one of claims 1 to 4, further comprising an X-ray imaging apparatus.

6. The region-in-object measuring system according to claim 5, wherein an X-ray camera is used for imaging instead of using an X-ray film.

7. The region-in-object measuring system according to claim 6, wherein a reference object has a square object surface frame and a square film frame or a film location reference frame in the same size.

8. A computing device for measuring a region-in-object comprising:

an input part which captures a two-dimensional X-ray image obtained by imaging a region-in-object by means of an X-ray imaging. apparatus in a state in which an object surface frame of a reference object is closely contacted with a surface of the object, the reference object having the object surface frame which is closely contacted with the surface of the object and a film frame which is closely contacted with an X-ray film, and the two frames being separated from each other;

a first computing part which determines a projection scaling factor for an image of the object surface frame based on the size of a predetermined pattern on a plane of the object surface frame and the size of an image of a predetermined pattern in a two-dimensional X-ray image;

a second computing part which determines a position vector of a specific point on the plane of the object surface frame and a position vector of an image of a specific point on the plane of the object surface frame in the two-dimensional X-ray image;

a third computing part which determines a position vector of an X-ray source based on the projection scaling factor determined by the first computing part and the position vector of the specific point on the plane of the object surface frame and the position vector of the image of the specific point on the plane of the object surface frame determined by the second computing part;

a fourth computing part which determines a position vector of an image of the region-in-object in the two-dimensional X-ray image; and a fifth computing part which determines a position vector of the region-in- object based on the position vector of the X-ray source determined by the third computing part and the position vector of the image of the region-in-object determined by the fourth computing part, and which decides an orientation of the region-in-object with respect to the image of the region-in-object.

9. A computing device for measuring a region-in-object comprising:

an input part which captures two or more two-dimensional X-ray images obtained by imaging a region-in-object from different directions by means of an X-ray imaging apparatus in a state in which an object surface frame of a reference object is closely contacted with a surface of the object, the reference object having the object surface frame which is closely contacted with the surface of the object and a film frame which is closely contacted with an X-ray film, and the two frames being separated from each other;

a first computing part which determines a projection scaling factor for an image of the object surface frame based on the size of a predetermined pattern on a plane of the object surface frame and the size of an image of a predetermined pattern in a two-dimensional X-ray image;

a second computing part which determines a position vector of a specific point on the plane of the object surface frame and a position vector of an image of a specific point on the plane of the object surface frame in the two-dimensional X-ray image;

a third computing part which determines a position vector of an X-ray source based on the projection scaling factor determined by the first computing part and the position vector of the specific point on the plane of the object surface frame and the position vector of the image of the specific point on the plane of the object surface frame determined by the second computing part;

a fourth computing part which determines a position vector of an image of the region-in-object in the two-dimensional X-ray image;

a fifth computing part which determines a position vector of the region-in-object based on the position vector of the X-ray source determined by the third computing part and the position vector of the image of the region-in-object determined by the fourth computing part; and a sixth computing part which decides a three-dimensional location of the region-in-object based on two or more of position vectors of the region-in-object determined by the fifth computing part.

10. A computing device for measuring a region-in-object comprising:

an input part which captures a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other;

a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient;

a second computing part which determines a projection scaling factor for the image of the object surface frame based on the size of a predetermined pattern on a plane of the object surface frame and the size of an image of a predetermined pattern on the reference plane;

a third computing part which determines a position vector of a specific point on the plane of the object surface frame and a position vector of an image of the specific point on the reference plane;

a fourth computing part which determines a location of an X-ray source vector based on the projection scaling factor determined by the second computing part and the position vector of a specific point on the plane of the object surface frame and the position vector of an image of the specific point on the reference plane determined by the third computing part;

a fifth computing part which determines a position vector of an image of the region-in-object on the reference plane; and a sixth computing part which determines a position vector of the region-in- object based on the location of the X-ray source vector determined by the fourth computing part and the position vector of the image of the region-in-object determined by the fifth computing part, and which decides an orientation of the region-in-object with respect to the location of the image region-in-object.

11. A computing device for measuring a region-in-object comprising:

an input part which captures two or more of a two-dimensional X-ray images obtained by imaging a region-in-object from different directions by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other;

a first computing part which determines a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient;

a second computing part which determines a projection scaling factor for the image of the object surface frame based on the size of a predetermined pattern on a plane of the object surface frame and the size of an image of a predetermined pattern on the reference plane;

a third computing part which determines a position vector of a specific point on the plane of the object surface frame and a position vector of an image of a specific point on the reference plane;

a fourth computing part which determines a location of an X-ray source vector based on the projection scaling factor determined by the second computing part and the position vector of a specific point on the plane of the object surface frame and the position vector of an image of the specific point on the reference plane determined by the third computing part;

a fifth computing part which determines a position vector of an image of the region-in-object on the reference plane;

a sixth computing part which determines a position vector of the region-in- object based on the location of the X-ray source vector determined by the fourth computing part and the position vector of the image of the region-in-object determined by the fifth computing part; and a seventh computing part which decides a three-dimensional location of the region-in-object based on two or more of position vectors of the region-in-object determined by the sixth computing part.

12. The computing device for measuring a region-in-object according to any one of claims 8 to 11, wherein data is used that is imaged using an X-ray camera instead of using an X-ray film.

13. A computer-readable medium having a program stored thereon for executing a computer to perform measuring region-in-object, comprising:

step A of accepting an input of a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface .of the object and a film frame which is closely contacted with an X-ray film, and the two frames being separated from each other;

step B of determining a projection scaling factor for an image of the object surface frame based on the size of a predetermined pattern on a plane of the object surface frame and the size of an image of a predetermined pattern in a two-dimensional X-ray image on the reference plane;

step C of determining a position vector of a specific point on the plane of the object surface frame and a position vector of an image of a specific point on the plane of the object surface frame in the two-dimensional X-ray image;

step D of determining a position vector of an X-ray source based on the projection scaling factor determined at step B and the position vector of the specific point on the plane of the object surface frame and the position vector of the image of the specific point on the plane of the object surface frame determined at step C;

step E of determining a position vector of an image of the region-in-object in the two-dimensional X-ray image; and step F of determining a position vector of the region-in-object based on the position vector of the X-ray source determined at step D and the position vector of the image of the region-in-object determined at step E, and determining an orientation of the region-in-object with respect to the image of the region-in-object.

14. A computer-readable medium having a program stored thereon for executing a computer to perform measuring region-in-object, comprising:

step A of accepting an input of two or more two-dimensional X-ray images obtained by imaging a region-in-object from different directions by means of an ray imaging apparatus in a state in which an object surface frame of a reference object is closely contacted with a surface of the object, the reference object having the object surface frame which is closely contacted with the surface of the object and a film frame which is closely contacted with an X-ray film, and the two frames being separated from each other;

step B of determining a projection scaling factor for an image of the object surface frame based on the size of a predetermined pattern on a plane of the object surface frame and the size of an image of a predetermined pattern in a two-dimensional X-ray image;

step C of determining a position vector of a specific point on the plane of the object surface frame and a position vector of an image of a specific point on the plane of the object surface frame in the two-dimensional X-ray image;

step D of determining a position vector of an X-ray source based on the projection scaling factor determined at step B and the position vector of the specific point on the plane of the object surface frame and the position vector of the image of the specific point on the plane of the object surface frame determined at step C;

step E of determining a position vector of an image of the region-in-object in the two-dimensional X-ray image;

step F of determining a position vector of the region-in-object based on the position vector of the X-ray source determined at step F and the position vector of the image of the region-in-object determined at step E; and step G of deciding a three-dimensional location of the region-in-object based on two or more of position vectors of the region-in-object determined at step F.

15. A computer-readable medium having a program stored thereon for executing a computer to perform measuring region-in-object, comprising:

step A of accepting an input of a two-dimensional X-ray image obtained by imaging a region-in-object by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other;

step B of determining a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient;

step C of determining a projection scaling factor for the image of the object surface frame based on the size of a predetermined pattern on a plane of the object surface frame and the size of an image of a predetermined pattern on the reference plane;

step ID of determining a position vector of a specific point on the plane of the object surface frame and a position vector of an image of the specific point on the reference plane;

step E of determining a location of an X-ray source vector based on the projection scaling factor determined at step B and the position vector of a specific point on the plane of the object surface frame and the position vector of an image of the specific point on the reference plane determined at step C;

step F of determining a position vector of an image of the region-in-object on the reference plane; and step G of determining a position vector of the region-in-object based on the location of the X-ray source vector determined step E and the position vector of the image of the region-in-object determined at step F, and deciding an orientation of the region-in-object with respect to the location of the image region-in-object.

16. A computer-readable medium having a program stored thereon for executing a computer to perform measuring region-in-object, comprising:

step A of accepting an input of two or more of a two-dimensional X-ray images obtained by imaging a region-in-object from different directions by means of an X-ray imaging apparatus in a state in which an object surface frame of a reference object is closely contacted with a surface of the object, the reference object having the object surface frame which is closely contacted with the surface of the object and a film location reference frame which is a reference of an X-ray film placed at a free location, and the two frames being separated from each other;

step B of determining a transformation coefficient for subjecting an image of the film location reference frame on the X-ray film to two-dimensional projection transformation into an image of the film location reference frame on a reference plane, that has to be taken in a state in which the X-ray film is closely contacted with the film location reference frame, and which subjects an image of the object surface frame on the two-dimensional X-ray image to two-dimensional projection transformation into an image of the object surface frame on the reference plane using the transformation coefficient;

step C of determining a projection scaling factor for the image of the object surface frame based on the size of a predetermined pattern on a plane of the object surface frame plane and the size of an image of a predetermined pattern on the reference plane;

step D of determining a position vector of a specific point on the plane of the object surface frame and a position vector of an image of a specific point on the reference plane;

step E of determining a location of an X-ray source vector based on the projection scaling factor determined at step C and the position vector of a specific point on the plane of the object surface frame and the position vector of an image of the specific point on the reference plane determined at step D;

step F of determining a position vector of an image of the region-in-object on the reference plane;

step G of determining a position vector of the region-in-object based on the location of the X-ray source vector determined at step E and the position vector of the image of the region-in-object determined at step F; and step H of deciding a three-dimensional location of the region-in-object based on two or more of position vectors of the region-in-object determined at step G.

17. The computer-readable medium according to any one of claims 13 to 16, wherein data is used that is imaged using an X-ray camera instead of using an X-ray film.

* * * * *